United States Patent
Kim et al.

(10) Patent No.: US 10,495,609 B2
(45) Date of Patent: Dec. 3, 2019

(54) ULTRASONIC INSPECTION TECHNIQUE TO ASSESS BOND QUALITY IN COMPOSITE STRUCTURES

(71) Applicant: The Aerospace Corporation, El Segundo, CA (US)

(72) Inventors: Yong Min Kim, Torrance, CA (US); Joseph T Case, Hawthorne, CA (US); Shant Kenderian, Pasadena, CA (US)

(73) Assignee: The Aerospace Corporation, El Segundo, CA (US)

( * ) Notice: Subject to any disclaimer, the term of this patent is extended or adjusted under 35 U.S.C. 154(b) by 557 days.

(21) Appl. No.: 15/296,958

(22) Filed: Oct. 18, 2016

(65) Prior Publication Data
US 2018/0106765 A1 Apr. 19, 2018

(51) Int. Cl.
| | | |
|---|---|---|
| G01N 29/06 | (2006.01) | |
| G01N 29/07 | (2006.01) | |
| G01N 29/48 | (2006.01) | |
| G01N 29/44 | (2006.01) | |
| G01N 29/04 | (2006.01) | |
| G01N 29/11 | (2006.01) | |

(52) U.S. Cl.
CPC ......... *G01N 29/069* (2013.01); *G01N 29/043* (2013.01); *G01N 29/07* (2013.01); *G01N 29/11* (2013.01); *G01N 29/4454* (2013.01); *G01N 29/48* (2013.01); *G01N 2291/012* (2013.01); *G01N 2291/015* (2013.01); *G01N 2291/0231* (2013.01); *G01N 2291/0289* (2013.01); *G01N 2291/044* (2013.01); *G01N 2291/267* (2013.01)

(58) Field of Classification Search
CPC .. G01N 20/069; G01N 29/11; G01N 29/4454; G01N 29/48; G01N 2291/012; G01N 2291/015; G01N 2291/0231; G01N 2291/0289; G01N 2291/044; G01N 29/069; G06T 7/0004; G06T 7/0008; G06T 2207/10136; G06T 2207/30164
USPC .................................. 73/602, 615, 627, 588
See application file for complete search history.

(56) References Cited

U.S. PATENT DOCUMENTS

| | | | | |
|---|---|---|---|---|
| 6,234,025 B1 * | 5/2001 | Gieske et al. | ....... | G01N 29/221 73/629 |
| 7,933,027 B1 * | 4/2011 | Roth | .................. | G01B 11/0625 356/27 |

OTHER PUBLICATIONS

C. Zhu et al., "Algorithm 778: L-BFGS-B: Fortran subroutines for large-scale bound-constrained optimization," ACM Trans. Math. Softw., vol. 23, No. 4, pp. 550-560, Dec. 1997.
(Continued)

*Primary Examiner* — Andrew W Johns
(74) *Attorney, Agent, or Firm* — LeonardPatel PC

(57) ABSTRACT

An ultrasonic inspection technique may be used to inspect quality of a bond between thermal protection system (TPS) material and a composite. The technique may include a highly damped transducer emitting an incident wave, which may traverse through thermal protection system (TPS) material and to a back wall of a composite. The incident wave may be of a low frequency signal, and may return a bondline echo and a backwall echo. The bondline echo is returned when the incident wave reaches a bondline and the backwall echo is returned when the incident wave reaches the backwall of the composite. The bondline echo and the backwall echo may be used to generate a waveform to assess the bond quality, revealing possible unbonds or kissing unbonds.

20 Claims, 23 Drawing Sheets
(8 of 23 Drawing Sheet(s) Filed in Color)

(56) References Cited

OTHER PUBLICATIONS

"Dlib C++ Library." [Online]. Available: http://dlib.net/, dated Oct. 11, 2016.

J. Keiner, "NFFT 3.0—Tutorial," Chemnitz Univ. Technol. Dep . . . , pp. 1-39, 2009.

M. Soumekh, "A system model and inversion for synthetic aperture radar imaging.," IEEE Trans. Image Process., vol. 1, No. I, pp. 64-76, 1992.

D. M. Sheen et al., "Three-dimensional millimeter-wave imaging for concealed weapon detection," IEEE Trans. Microw. Theory Tech., vol. 49, No. 9, pp. 1581-1592, 2001.

J. T. Case et al., "Optimum Two-Dimensional Uniform Spatial Sampling for Microwave SAR-Based NDE Imaging Systems," IEEE Trans. Instrum. Meas., vol. 60, No. 12, pp. 3806-3815, Dec. 2011.

B. Subiza et al., "An approach to SAR imaging by means of non-uniform FFTs," IGARSS 2003. 2003 IEEE Int. Geosci. Remote Sens. Symp. Proc. (IEEE Cat. No. 03CH37477), vol. 6, No. 3, pp. 0-2, 2003.

J. M. Lopez-Sanchez et al., "3-D Radar Imaging Using Range Migration," IEEE Trans. Antennas Propag., vol. 48, No. 5, pp. 728-737, 2000.

J. T. Case et al., "Nonuniform Manual Scanning for Rapid Microwave Nondestructive Evaluation Imaging", IEEE Trans. Instrum. Meas., 2012.

\* cited by examiner

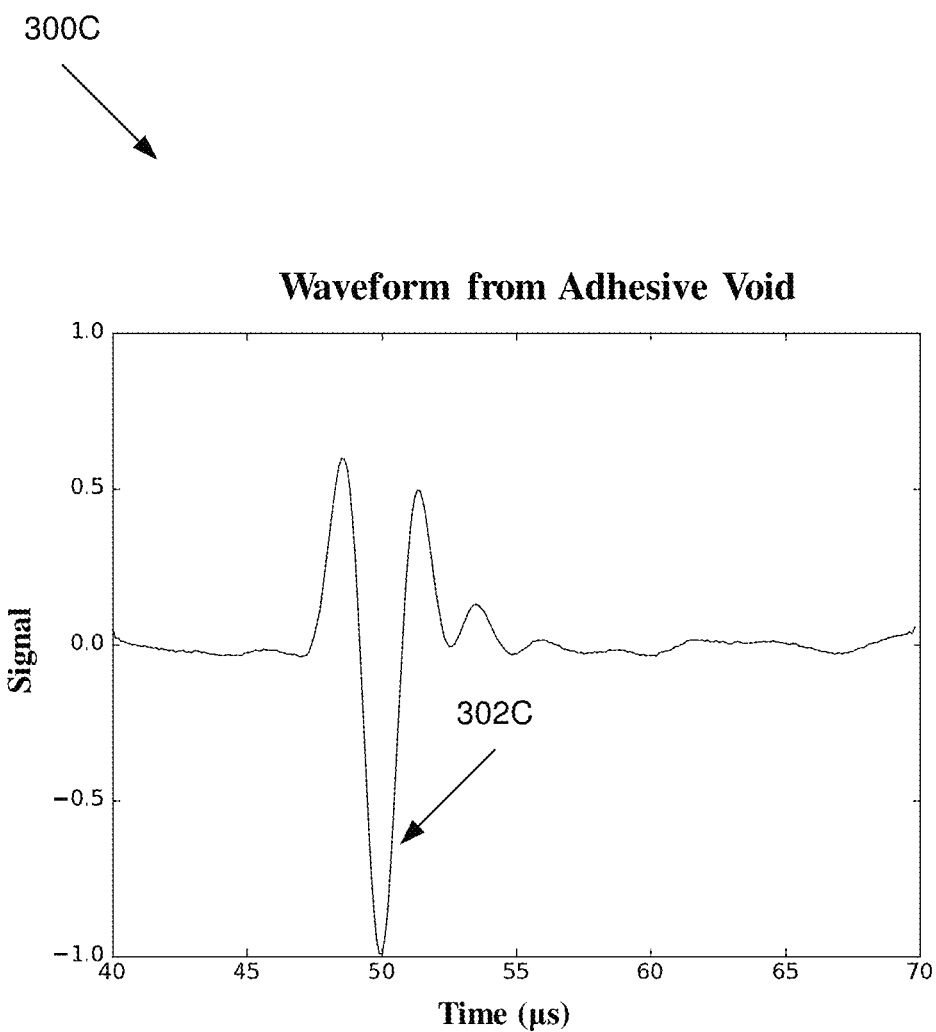

Fig. 5
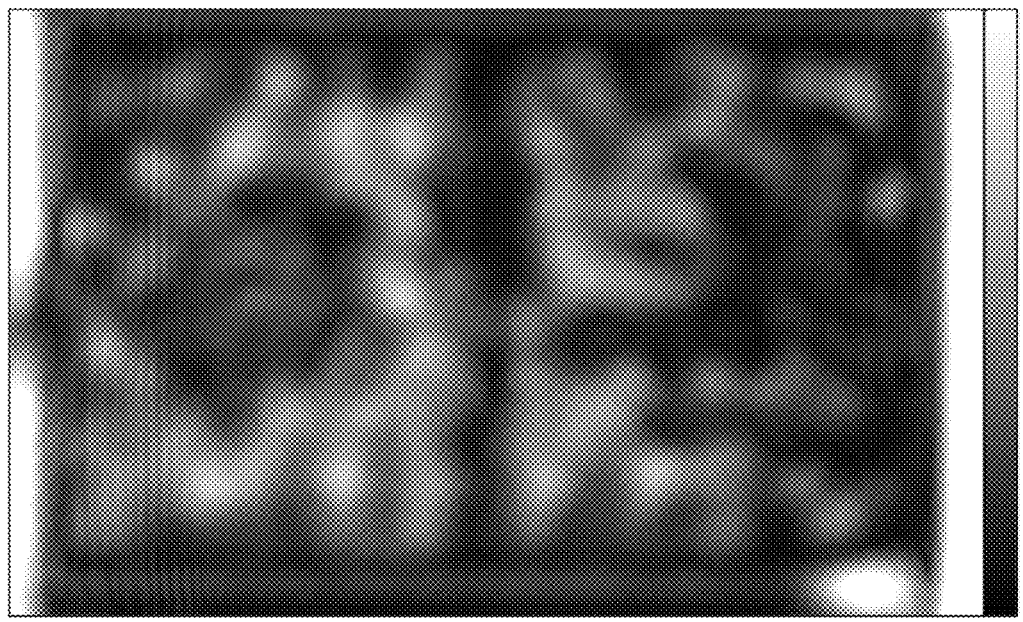

1100

1200

1300

Fig. 14
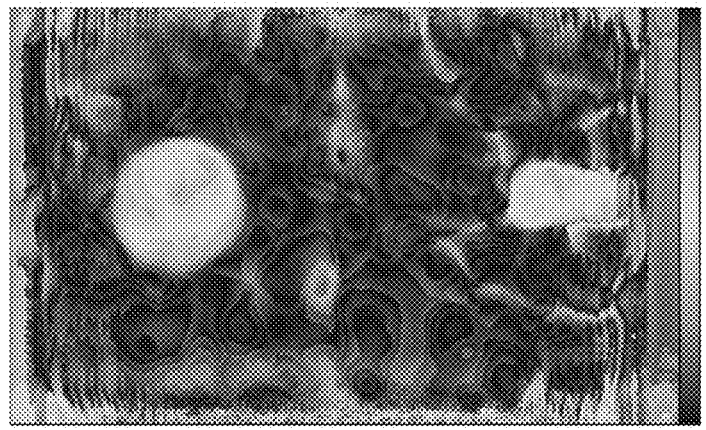

Fig. 15
1500

1600

Fig. 17
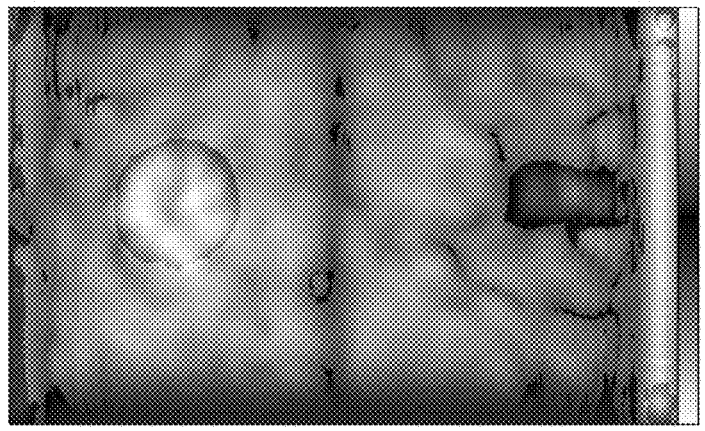

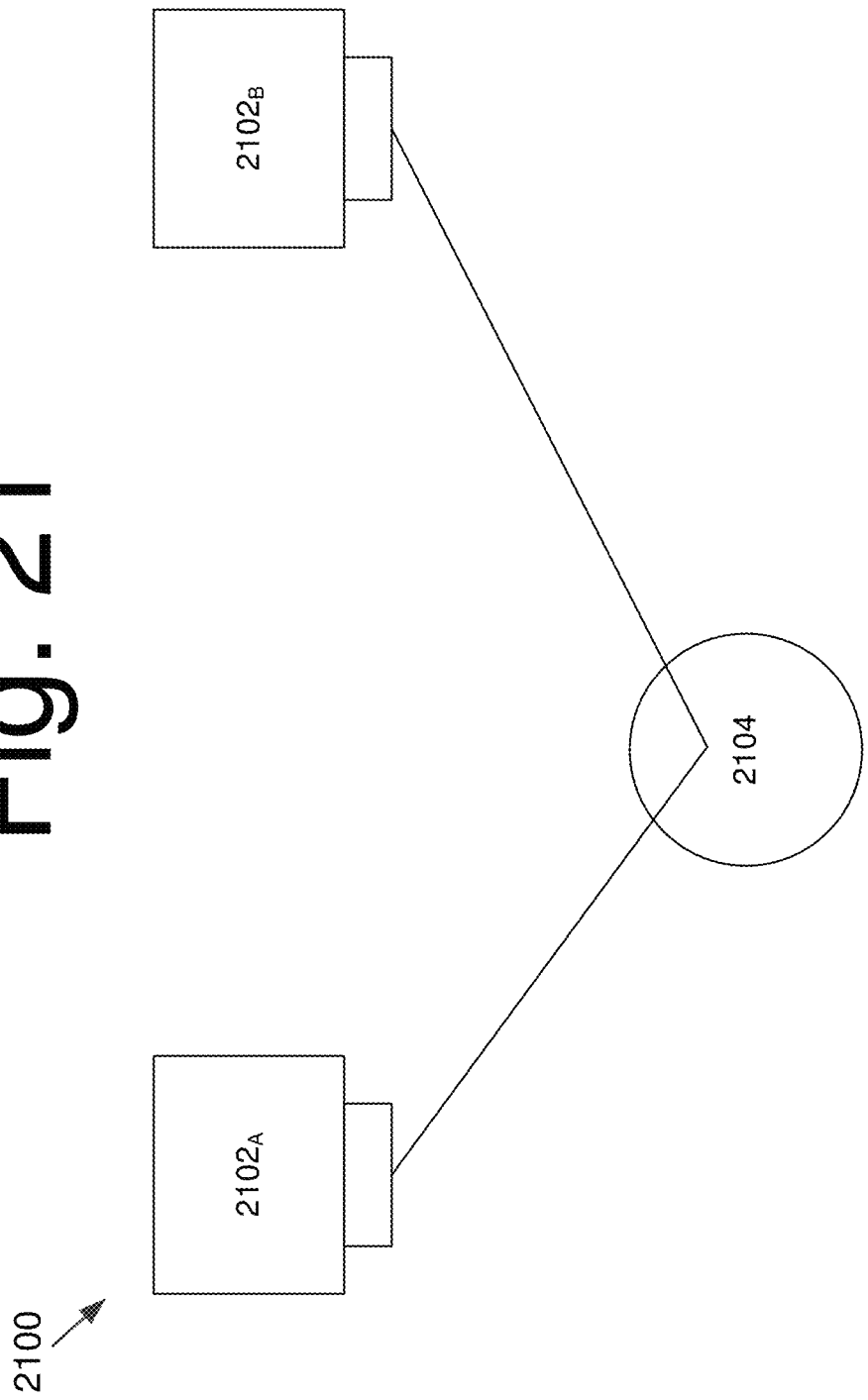

ULTRASONIC INSPECTION TECHNIQUE TO ASSESS BOND QUALITY IN COMPOSITE STRUCTURES

STATEMENT OF GOVERNMENT INTEREST

This invention was made with government support under Contract No. NNL11AA01B awarded by the National Aeronautics and Space Administration. The government has certain rights in the invention.

FIELD

The present invention generally pertains to the inspection of a bonded interface, and more particularly, to inspecting bonds between thick, dissimilar, attenuative, or scattering materials using ultrasound technology.

BACKGROUND

The bottom surface of a capsule, such as the Orion capsule, becomes extremely hot upon reentry into the Earth's atmosphere. To protect the capsule, the bottom surface is covered with a thermally resistant material known as a thermal protection system (TPS).

By its very nature, when entering the Earth's atmosphere, the TPS material absorbs vibration, and therefore, absorbs sound. This imposes added difficulties during inspection of the heat shield blocks that are bonded to the composite (e.g., blocks bonded to the bottom surface of the capsule). Additional difficulties include the fact that the TPS material is relatively low in density, has mechanical damping, is thermally insulated, and is inhomogeneous. Because the TPS material absorbs heat, thermal technologies cannot be used to inspect the bonded interface between the TPS material and the composite. Also, because inspection may be performed from only the outer surface of the TPS material, conventional inspection technologies, such as x-ray technology, cannot be used to inspect the bonded interface since the x-ray source and detector must be placed on opposite sides of the TPS.

Furthermore, it is imperative that the technique detects kissing unbonds. A kissing unbond is defined as two surfaces that are in contact, but are not actually bonded. Electromagnetic technologies, such as x-ray and terahertz technologies, may be used to detect changes in the bondline, such as air gaps. However, electromagnetic technologies cannot differentiate between bond and unbond conditions when an air gap is missing. Consequently, electromagnetic technologies cannot detect kissing unbonds.

Thus, inspection of the bonded interface may be complex, and an improved approach is desirable.

SUMMARY

Certain embodiments of the present invention may be implemented and provide solutions to the problems and needs in the art that have not yet been fully solved by conventional bond inspection technologies. For example, some embodiments pertain to ultrasonic inspection techniques to assess the bond quality between the TPS material and the composite.

In an embodiment, an apparatus for inspecting a bond quality may include a highly damped transducer emitting an incident wave that traverses through the TPS material and reflects from the back wall of a composite. The incident wave is a low frequency signal. The incident wave returns a bondline echo when the incident wave reaches a bondline. The incident wave also returns a backwall echo when the incident wave reaches the backwall of the composite.

In another embodiment, a process includes using a transducer to emit an incident wave, resulting in a return of a bondline echo from a bondline and a backwall echo from a backwall of a composite. The process further includes generating a waveform from the bondline echo and the backwall echo, and performing additional processing techniques to generate an image of a bond between a TPS material and the composite, showing a quality of the bond.

In yet another embodiment, a hand-held scanning system for assessing the quality of a bond between a thermal protection system (TPS) and a composite is provided. The hand-held scanning system includes a set of encoders connected to a highly damped transducer. The highly damped transducer may scan the TPS, which has a flat surface, curved surfaces, or both, for purposes of assessing the bond quality. The system also includes a computing system configured to receive the scanned data and generate a waveform, one or more images, or both, revealing a map of the quality of the bond.

BRIEF DESCRIPTION OF THE DRAWINGS

The patent or application file contains at least one drawing executed in color. Copies of this patent or patent application publication with color drawing(s) will be provided by the Office upon request and payment of the necessary fee. In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIGS. 3A-3C are graphs illustrating waveforms of various flawed regions, according to an embodiment of the present invention.

FIG. 5 illustrates an image showing a magnitude of a backwall echo (M2), according to an embodiment of the present invention.

FIG. 14 illustrates an image after SAFT of the phase of bondline echo (P1), according to an embodiment of the present invention.

FIG. 15 illustrates an image after SAFT of the phase cosine of a bondline echo (Cos P1), according to an embodiment of the present invention.

FIG. 17 illustrates an image after SAFT of the weighted phase by the bondline echo magnitude, according to an embodiment of the present invention.

FIG. 21 is a diagram illustrating a hand-held scanning system, according to an embodiment of the present invention.

DETAILED DESCRIPTION OF THE EMBODIMENTS

Some embodiments of the present invention pertain to an ultrasonic inspection technique to assess bond quality in composite structures. While TPS material is difficult to inspect using ultrasonic testing (UT) due to inhomogeneity, scattering, and absorption, some embodiments described herein use low frequency UT.

Low frequency UT may penetrate into TPS material with high damping, resulting in the assessment of the bond quality. Because TPS material does not absorb lower frequency sound, but does absorb higher frequency sound, a lower frequency transducer may be used to improve penetration into the TPS material. As lower frequency is used, the wavelength becomes longer, resulting in a loss of resolution in the time domain. Furthermore, with lower frequency, a larger transducer is required, resulting in a loss of resolution in the spatial domain.

To resolve these issues, the time resolution and spatial resolution should be improved. The technique to improve time resolution and spatial resolution used in some embodiments is discussed in more detail below.

In some embodiments, a highly damped transducer and SAFT processing may be used to improve the time resolution and the spatial resolution, respectively.

Figure 1:
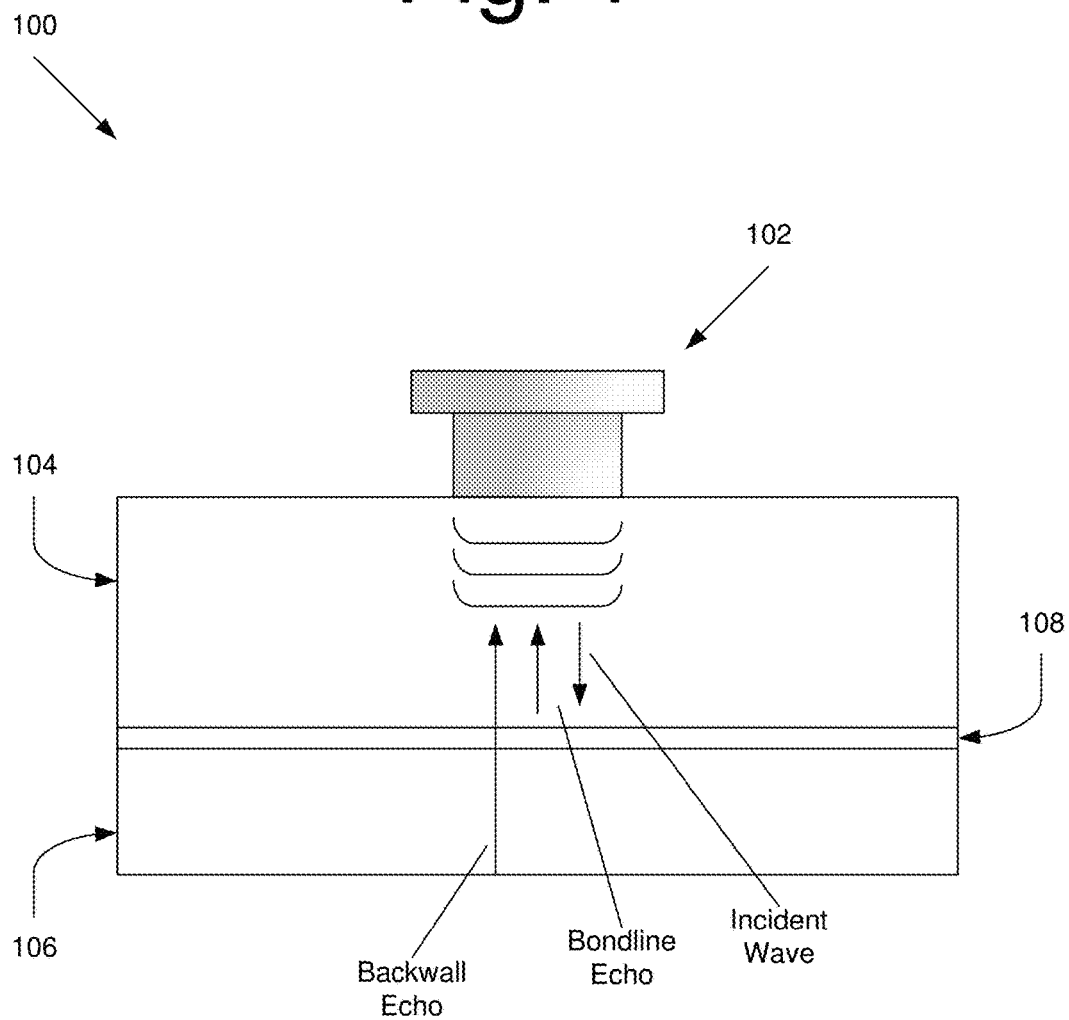
FIG. 1 illustrates an ultrasonic inspection technique using a transducer, according to an embodiment of the present invention.

In order to select the transducer, frequency, size of transducer, pulse shape, and damping may be considered. FIG. 1 illustrates an ultrasonic inspection technique using a transducer 102, according to an embodiment of the present invention. In an embodiment, transducer 102 with high damping is used to improve the time resolution issue discussed above since a highly damped transducer has a shorter pulse in time. For example, transducer 102 may be positioned next to a bottom surface of a spacecraft. The bottom surface may include TPS material 104 and composite 106. Bondline 108 shows the bond between TPS material 104 and composite 106.

In order to interrogate the bond condition, i.e., determine whether an air gap or an unbond exists in bondline 108, transducer 102 may be moved along any area of TPS material 104. For example, transducer 102 emits an incident wave (or sound) that is of a short time duration. The incident wave may penetrate through bondline 108 and composite 106, resulting in a return of a first echo (or bondline echo) and a second echo (or backwall echo). For purposes of explanation, the backwall echo may be a signal that is returned from the back wall of composite 106.

Simply put, the incident wave is a pulse-like signal rather than a resonating signal, allowing different interfaces, which are close to each other, to be distinguished on a computing device, for example.

One of ordinary skill in the art may readily appreciate that transducer 102 may be moved in any direction along TPS material 104. This way, a thorough scan of bondline 108 may be realized, and a waveform of bondline 108 may be generated on a computing system for analysis, for example. This may also allow an operator to generate a larger image of the entire bondline 108 using the various techniques described below.

Figure 2:
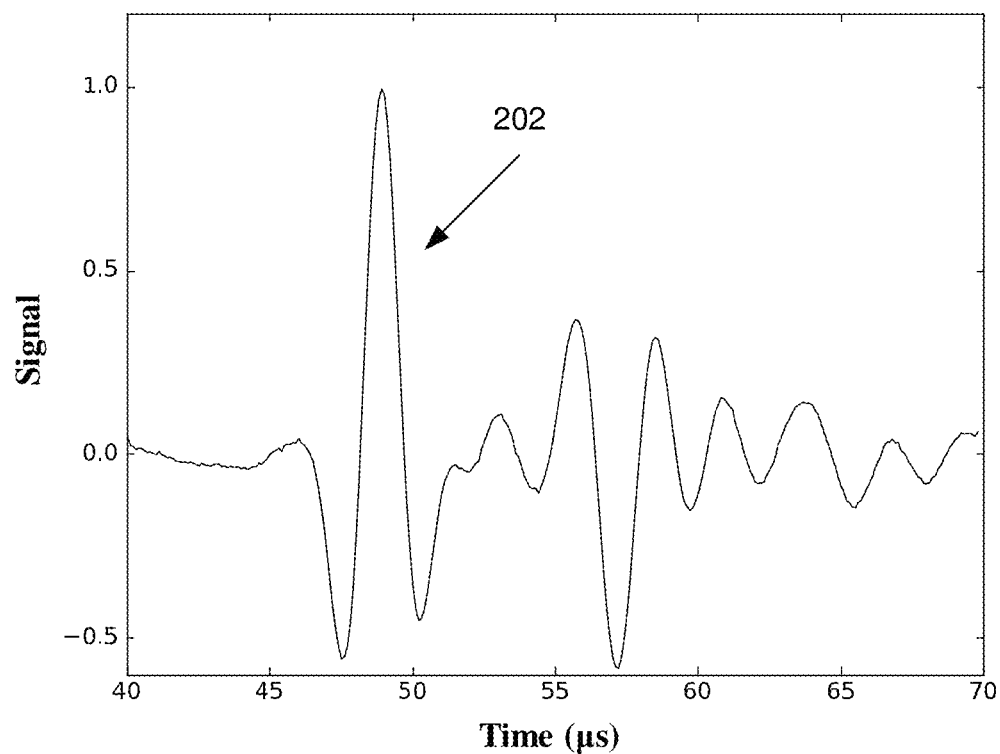
FIG. 2 is a graph illustrating a waveform of a bondline echo and a backwall echo, according to an embodiment of the present invention.

FIG. 2 is a graph 200 illustrating a waveform 202 of a bondline echo and a backwall echo, according to an embodiment of the present invention. In graph 200, the bondline echo and the backwall echo show that the scanned area reveals no air gaps or unbonds between the TPS material and the composite.

Figure 3A:
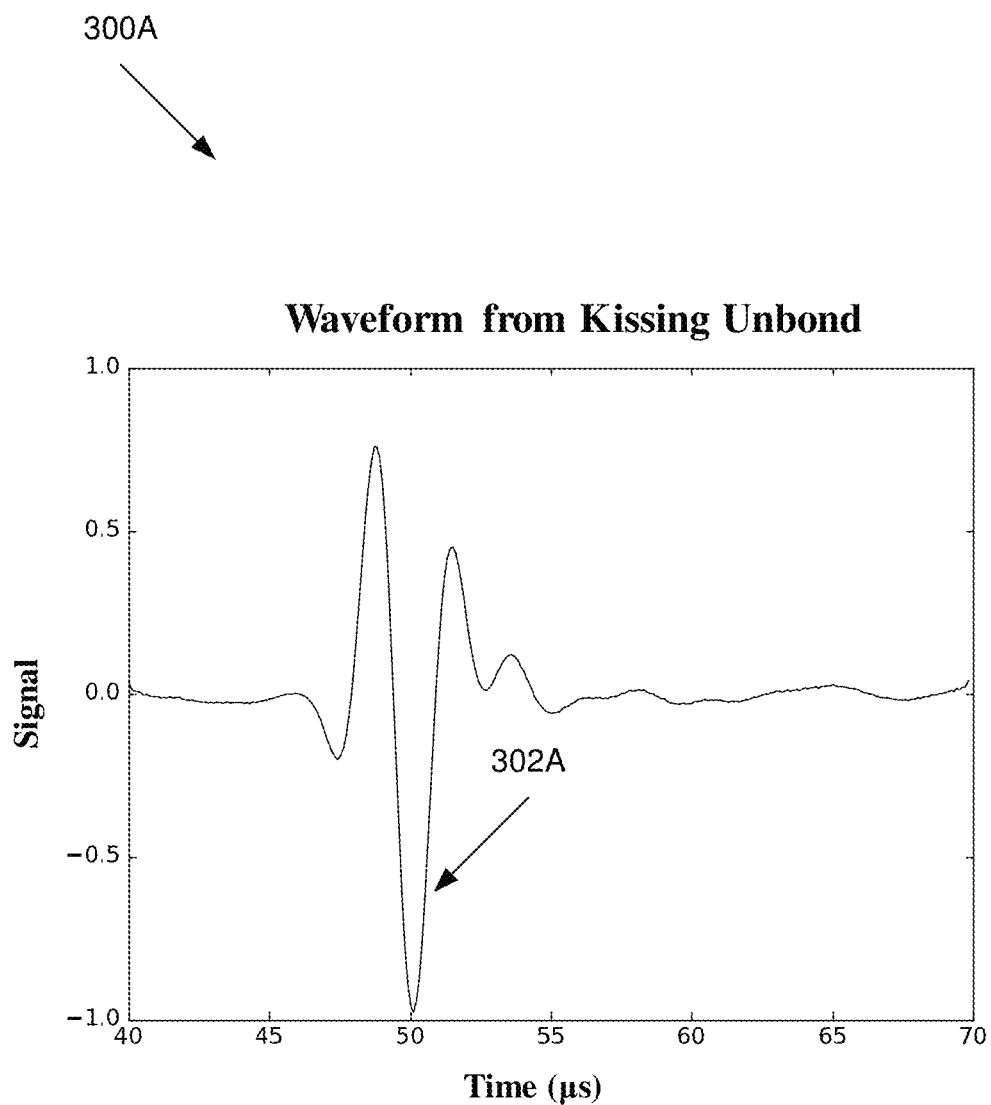
Figure 3B:
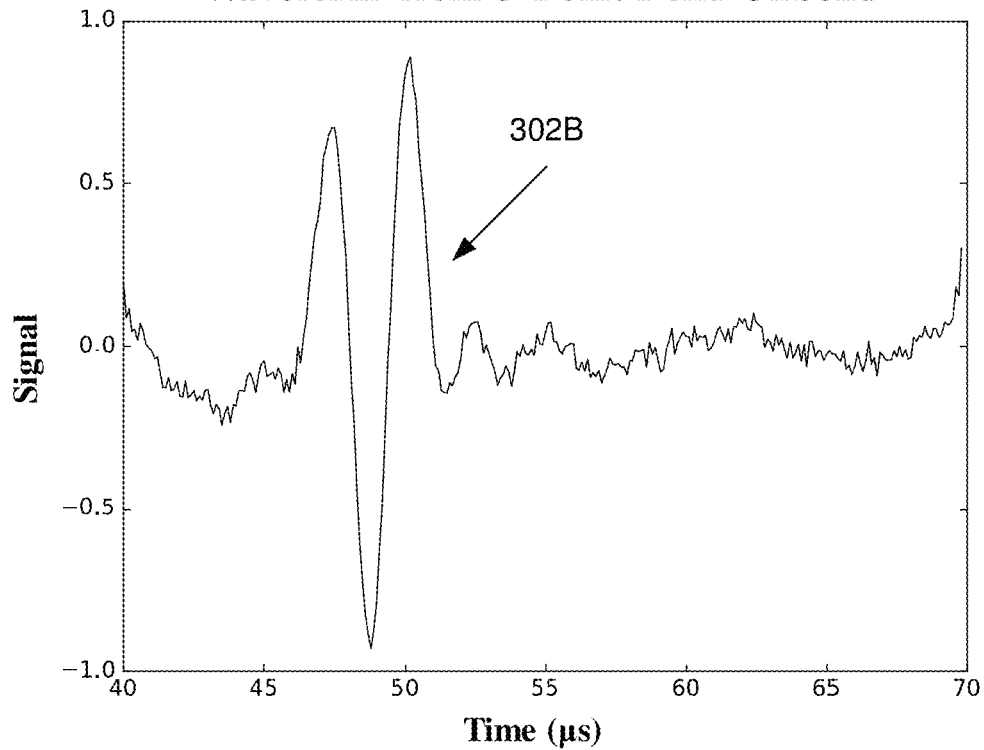

FIGS. 3A-3C, however, are graphs 300A, 300B, 300C illustrating waveforms 302A, 302B, 302C of various flawed regions, according to an embodiment of the present invention. For example, waveform 302A shows an echo identifying a kissing unbond, waveform 302B shows an echo identifying a 3-point bend debond, and waveform 302C shows an echo identifying an adhesive void. Consequently, all features represent unbond conditions. One of ordinary skill in the art would readily appreciate that the magnitude of the bondline echo in the waveforms varies greatly. However, echoes are consistent when regarding phase inversion and missing backwall echo.

Magnitude of Bondline Echo (M1) and Backwall Echo (M2)

Figure 4:
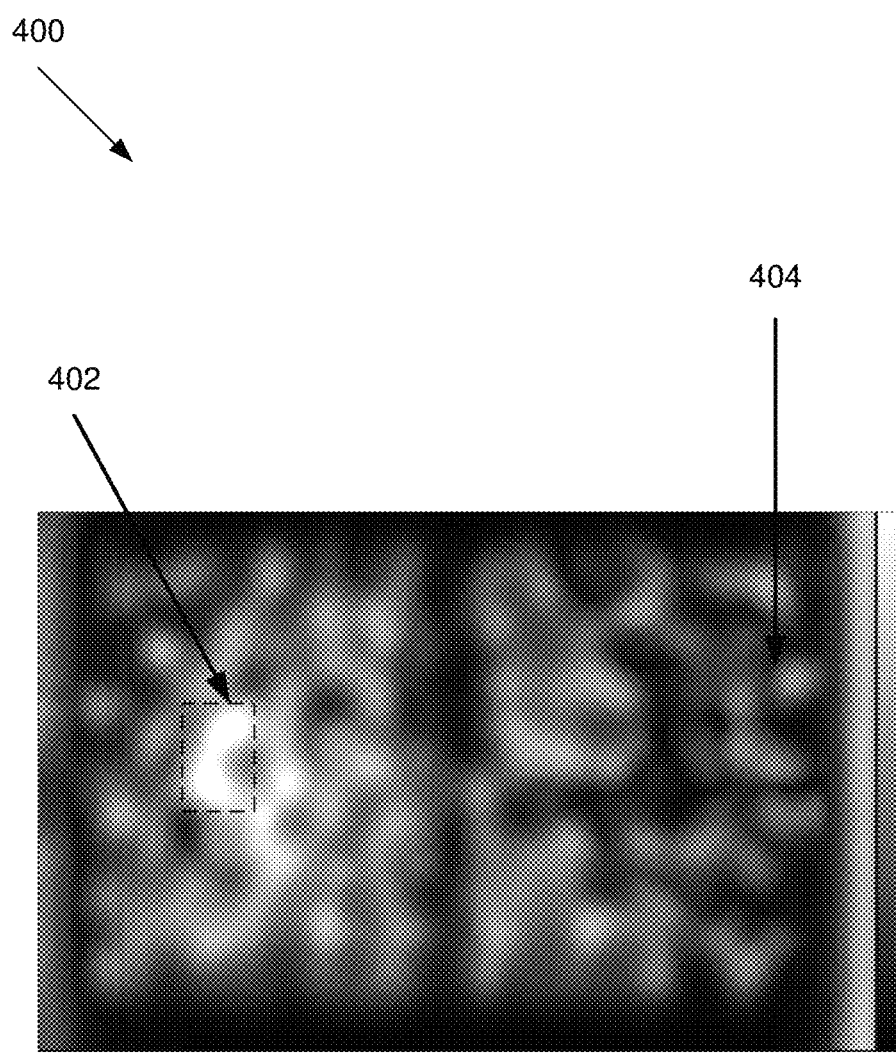
FIG. 4 illustrates an image showing a magnitude of a bondline echo (M1), according to an embodiment of the present invention.

FIG. 4 illustrates an image 400 showing a magnitude of a bondline echo (M1), and FIG. 5 illustrates an image 500 showing a magnitude of a backwall echo (M2). M1 and M2 were extracted from the magnitude of the complex analytic representation of the signal. Thus, M1 and M2 represent peak signal magnitude of the bondline and backwall echoes, respectively.

In FIG. 4, item 402 of image 400 reveals a kissing unbond in the bondline. The kissing unbond, item 402, is relatively brighter since most of the energy is returned from the bondline (i.e., earlier than the backwall). The pull tab, item 404, is arguably not visible. However, the later combination of these magnitudes M1 and M2 shown in FIG. 4 and FIG.

5, respectively, will make both unbonds visible, which may not have otherwise been visible using the conventional techniques discussed above.

Amplitude Ratio

By receiving the bondline echo and the backwall echo, additional signal processing techniques may be implemented to enhance the image for assessing the bond quality. For example, the bondline echo (M1) and the backwall echo (M2) may be gated separately and scanned with different gain settings.

It should be noted that variations in the TPS material at any one location may impact the signal strength of bondline echo (M1) and backwall echo (M2), equally. With this in mind, by taking the ratio of the signal amplitude between bondline echo (M1) and backwall echo (M2), the effect of inhomogeneity in the TPS material is neutralized, and the effect of defect areas, where one echo is impacted more than the other echo, may be highlighted. See, for example, FIG. 6, which illustrates an image 600 showing backwall echo (M2) to bondline echo (M1) ratio of magnitudes, according to an embodiment of the present invention. By dividing M2/M1, a grayscale image may be formed. A threshold may be applied to the grayscale image by the use of color to indicate that values below the threshold indicate unbond condition and are colored blue, and values above the threshold indicate a healthy bond and are colored gold. Using this technique, image 600 reveals a 2.5-inch kissing unbond in the dark blue region at 602 and a pull tab also in the dark blue region at 604.

Figure 6:
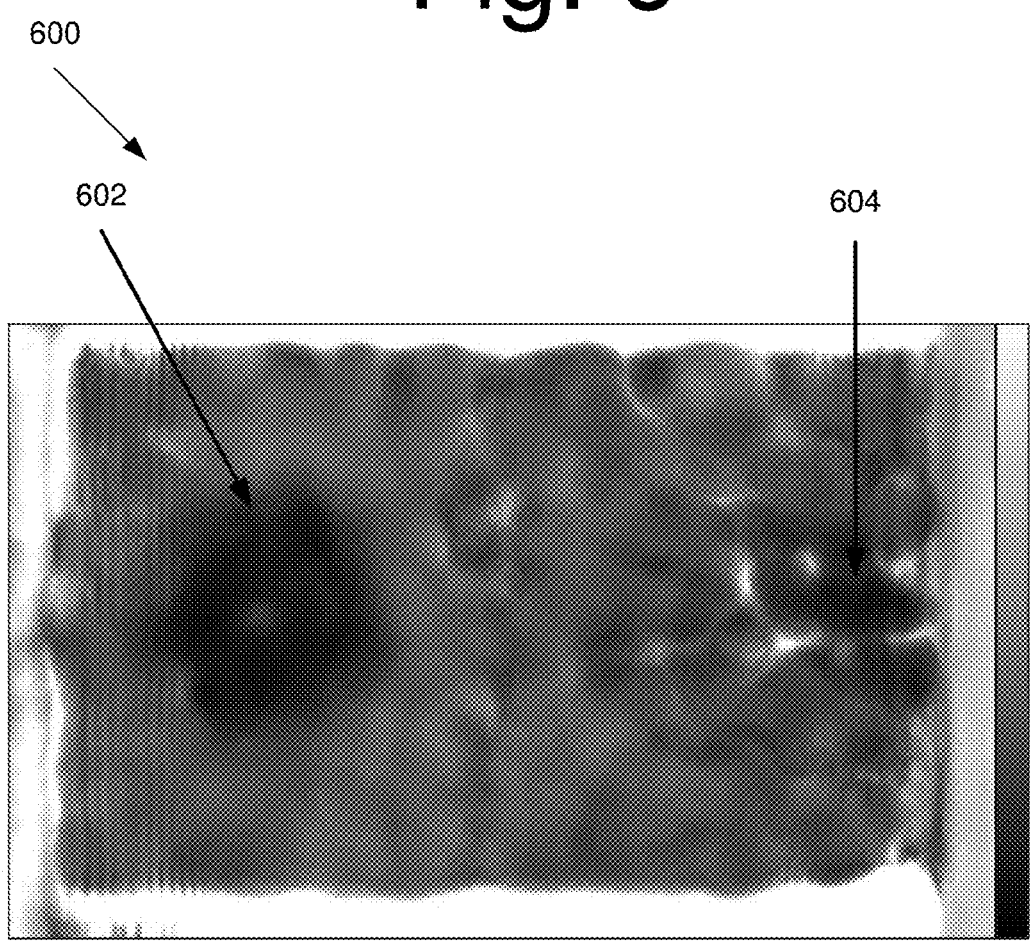
FIG. 6 illustrates an image showing backwall echo (M2) to bondline echo (M1) ratio of magnitudes, according to an embodiment of the present invention.

While the magnitude ratio, M2/M1, may be sufficient to observe on a grayscale image, a threshold criteria may be applied to the image to distinctly color unbonds as compared to bonds, as shown more clearly in FIG. 6.

Phase Scan

While the amplitude ratio technique discussed above provides images that are consistent with known defect regions, additional processing techniques may be applied. For example, while the amplitude of an echo from a disbonded interface may not always be a reliable reference, the phase of an echo may lead to a better understanding of the nature of the bond interface. For instance, when an echo propagates from a high impedance to a low impedance material (e.g., TPS material to air=unbond), the phase is reversed. When, however, the echo propagates from a low impedance to high impedance material (TPS to composite=bond), the phase is preserved. Since the TPS material and the composite are bonded, the impedance may shift from low to high. However, with the TPS material having a thin layer of air that is unbonded, the impedance may shift from high to low. Thus, steps to calculate the phase of the bondline echo (P1) may be taken. For instance, the phase of the bondline echo (P1) may be described by the phase of the complex analytic signal corresponding to the location of bondline echo (M1).

Figure 7:
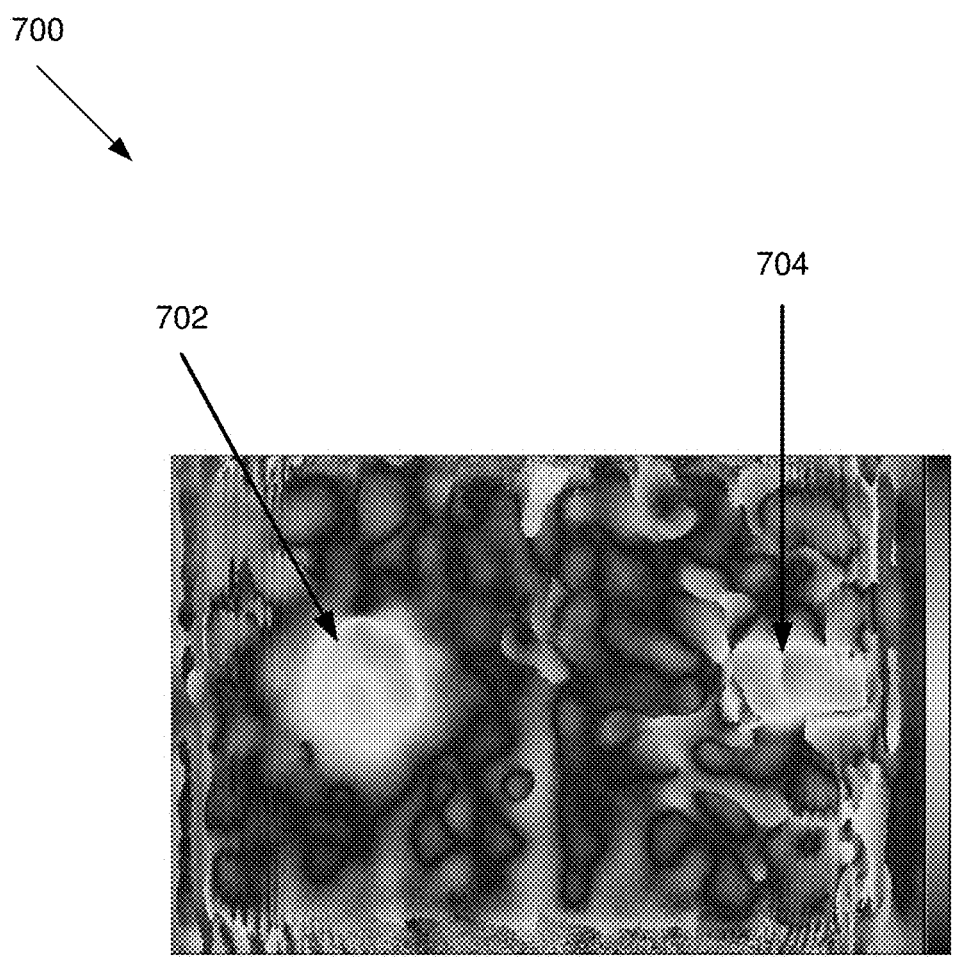
FIG. 7 illustrates an image showing a phase of bondline echo (P1), according to an embodiment of the present invention.

FIG. 7 illustrates an image 700 showing a phase of bondline echo (P1), according to an embodiment of the present invention. The phase of bondline echo (P1) in image 700 reveals a 2.5-inch kissing unbond at item 702 and a pull tab at item 704. It should be appreciated that in some embodiments a custom scale may be built to represent a range of $-\pi$ to $+\pi$, where $-\pi$ is equal to $+\pi$.

The phase color map for FIG. 7 was chosen in this embodiment so that each coordinate direction in the complex plane (i.e., phase of 0, $\pi/2$, $\pi$, and $-\pi/2$) has its own color. Consequently, the phases of 0 and $\pi$ are represented by complementary colors. In this embodiment, the phase of 0 is colored blue, $\pi/2$ is colored magenta, $\pi$ is colored yellow, and $-\pi/2$ is colored green.

Because the phase may rotate freely and may be ambiguous, it may be beneficial to take the cosine of the phase in some embodiments. This is because everything that is positive may be identified as good and everything that is negative may be identified as bad. By implementing the cosine of the phase of the bondline echo (Cos P1), a black and white image of the bondline echo is realized.

Figure 8:
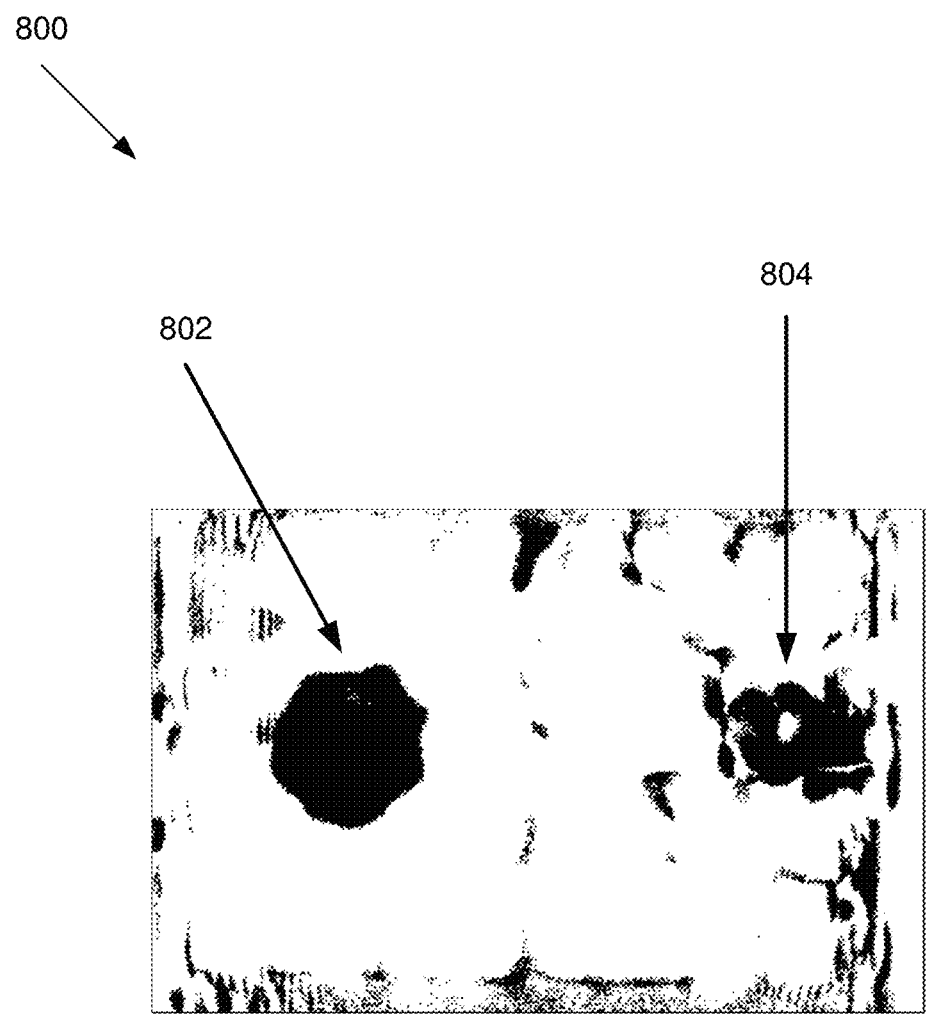
FIG. 8 illustrates an image of a phase cosine of a bondline echo (Cos P1), according to an embodiment of the present invention.

FIG. 8 illustrates an image 800 of the cosine of the phase of the bondline echo (CosPD, according to an embodiment of the present invention. By taking the cosine of the phase map, values are converted in this embodiment to a $-1$ to $+1$ range. Also, by setting a threshold at 0, the phase map shown in FIG. 7 is now converted to a black and white representation of the reversed phase versus preserved phase. The cosine of the phase of the bondline echo (Cos P1) in image 800 of FIG. 8 reveals a 2.5-inch kissing unbond in the black region at item 802 and a pull tab at item 804.

Weighted Phase Scan

Because the bondline echo and/or the backwall echo is either weak or strong, the phase confidence in the measurement is also weak or strong. For example, a weak signal may result in a weak confidence. In some embodiments, the phase scan may be multiplied by the bondline signal amplitude resulting in a weighted phase scan.

Figure 9:
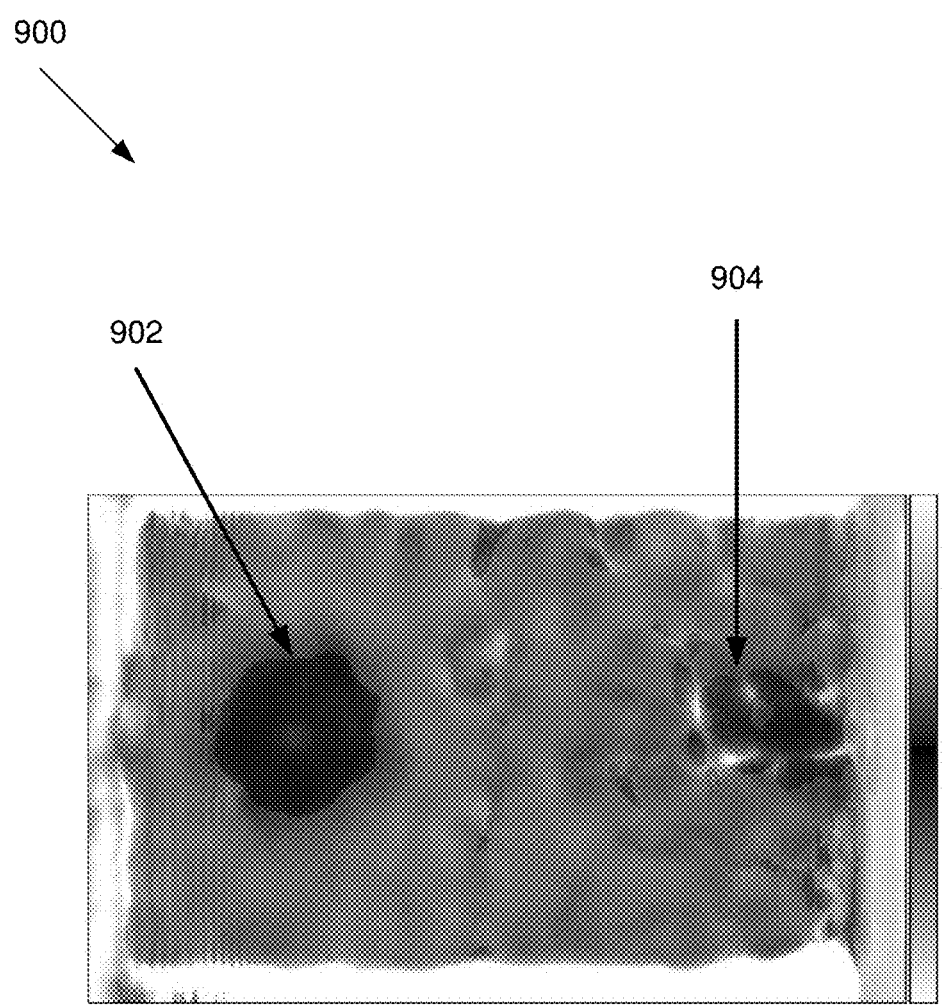
FIG. 9 illustrates an image of a weighted phase by the ratio of magnitudes, according to an embodiment of the present invention.

FIG. 9 illustrates an image 900 of a weighted phase by bondline echo magnitude ratio, according to an embodiment of the present invention. The weighted phase in some embodiments is (M2/M1)*(Cos P1). By implementing the weighted phase, a 2.5-inch kissing unbond in the dark blue region, at item 902, and a pull tab, at item 904, are revealed. The dark blue indicates weak (M2/M1) with negative Cos P1. By contrast, bonded regions are bright and red, indicating strong (M2/M1) with positive Cos P1.

Figure 10:
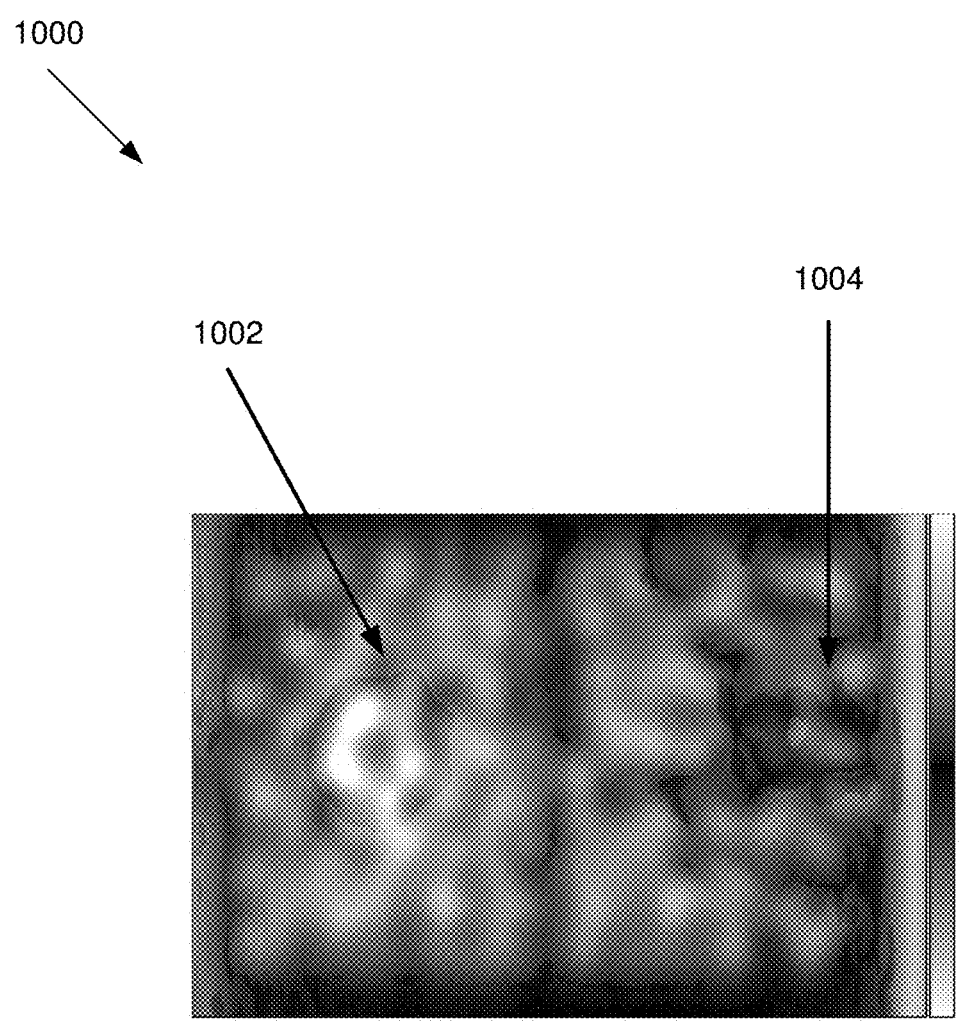
FIG. 10 illustrates an image of a weighted phase by the bondline echo magnitude, according to an embodiment of the present invention.
Figure 11:
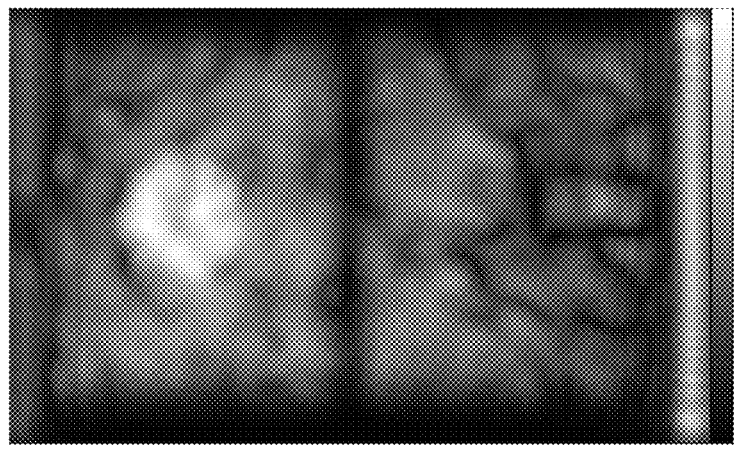
FIG. 11 illustrates an image after synthetic aperture focusing technique (SAFT) of the magnitude of the bondline echo (M1), according to an embodiment of the present invention.
Figure 12:
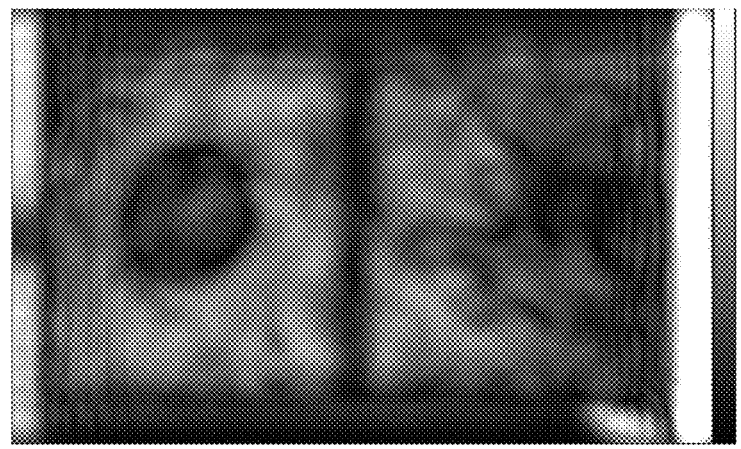
FIG. 12 illustrates an image after SAFT of the magnitude of the backwall echo (M2), according to an embodiment of the present invention.
Figure 13:
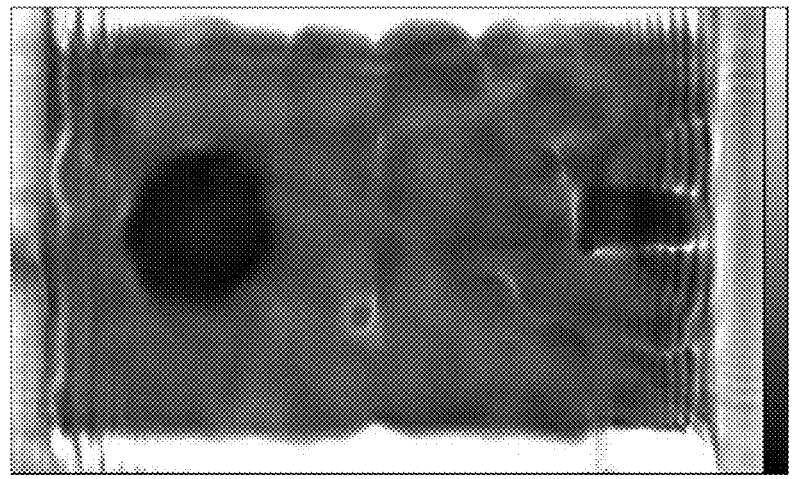
FIG. 13 illustrates an image after SAFT of the backwall echo (M2) to bondline echo (M1) ratio of magnitudes, according to an embodiment of the present invention.
Figure 16:
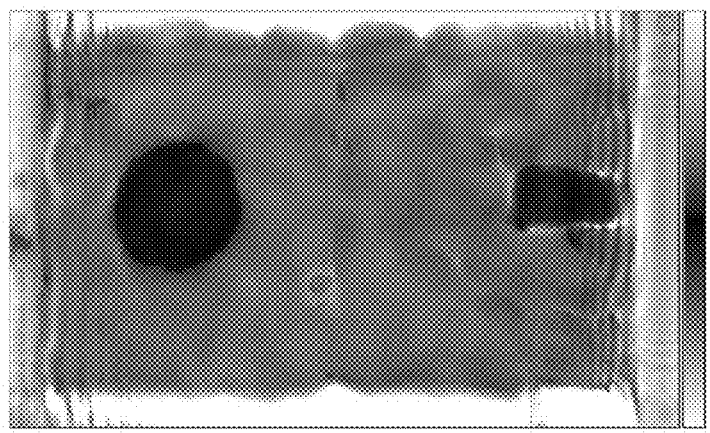
FIG. 16 illustrates an image after SAFT of the weighted phase by the ratio of magnitudes, according to an embodiment of the present invention.

FIG. 10 illustrates an image 1000 of a weighted phase by the bondline echo magnitude (M1), according to an embodiment of the present invention. The weighted phase in some embodiments is (M1)*(Cos P1). Certain embodiments may use color to intelligently render this information into an image. For example, blue indicates negative Cos P1 and unbond, and red indicates positive Cos P1 and bond. The magnitude of M1 is indicated by the intensity, thus high magnitude also indicates confidence in phase measurement. By rendering the information in this fashion, the weighted phase reveals a 2.5-inch kissing unbond in the bright blue region at item 1002 and a pull tab in a dark blue region at item 1004. By contrast, bonded regions are bright and red.

SAFT

To improve on spatial resolution, SAFT may be used. For example, when the transducer, as shown in FIG. 1, traverses across a defect bondline, the transducer may detect a reversal in the phase of the reflected signal. When the transducer is halfway across this bondline, the phase reversal amounts to complete destructive interference. This interference may result in a well-defined outline of the defect area as viewed under a magnitude of the bondline scan.

Thus, by using SAFT, a focusing effect may be created based on the fact that a large transducer with a diverging beam detects each point on the same plane from multiple locations.

FIGS. 11-17 illustrate images 1100-1700 after SAFT is applied for the bondline echo, backwall echo, amplitude ratio, phase of bondline echo, cosine of phase of bondline echo, weighted phase by ratio of amplitudes, and weighted phase by bondline echo magnitude, respectively.

Images resulting from using SAFT generally have higher spatial resolution and higher image contrast. The higher image contrast is particularly useful when deducing the size of unbonds from the magnitude ratio (M2/M1).

Figure 18:
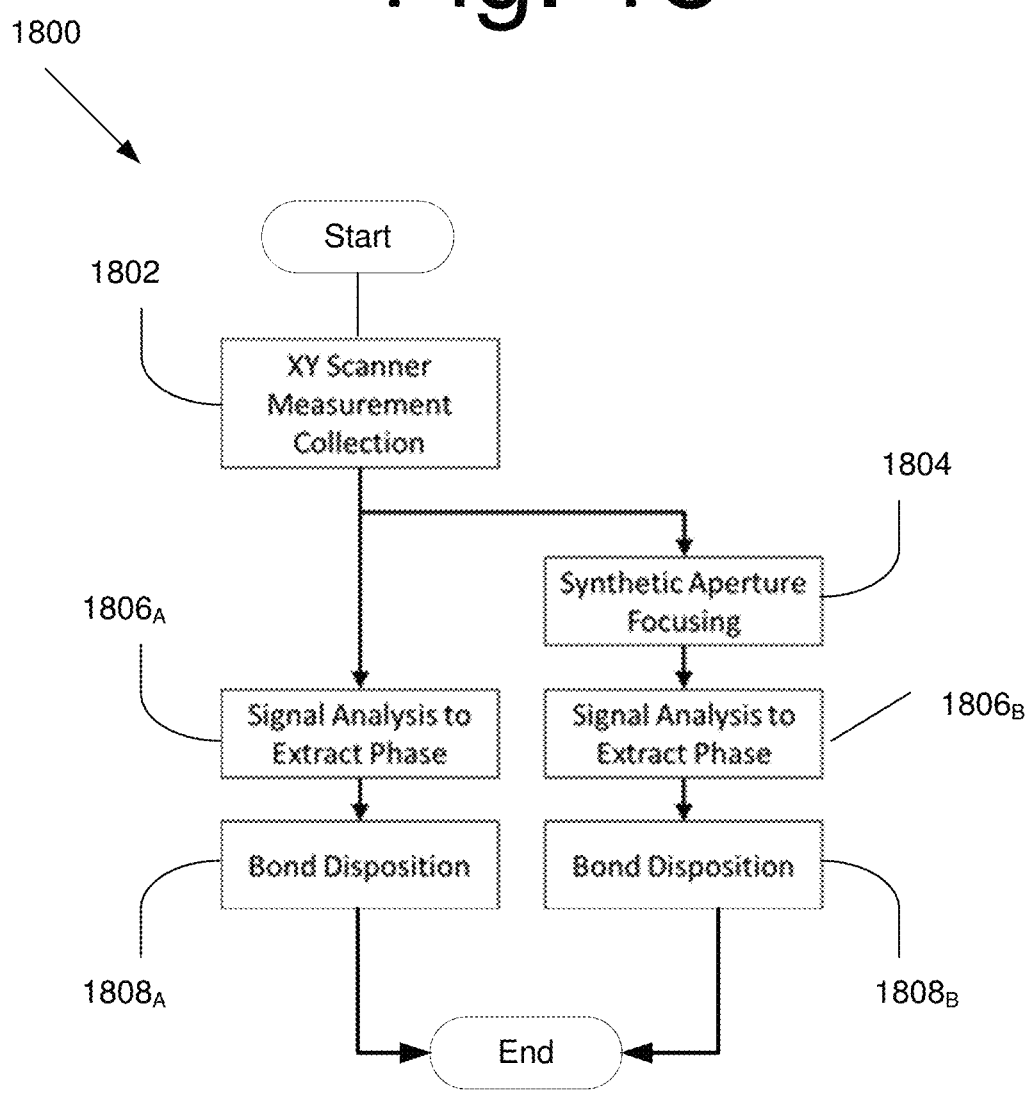
FIG. 18 is a flow diagram illustrating a process for UT bond testing, according to an embodiment of the present invention.

FIG. 18 is a flow diagram illustrating a process 1800 for UT bond testing, according to an embodiment of the present invention.

Process 1800 begins at 1802 with an XY scanner collecting measurement data for a bondline between the TPS material and the composite. The XY scanner in some embodiments includes a 2-dimensional (2D) scanner with an attached low-frequency, highly damped transducer used for bond testing. The UT probe may be focused or unfocused depending on the embodiment. The sample to be tested may be in a water bath for an immersion scan or the transducer may be configured for contact measurement.

Moreover, the measurement data may be collected by a raster scan (e.g., automated uniform spatial sampling density) in some embodiments. In other embodiments, the measurement data may be collected by a hand-scan (e.g., manual non-uniform spatial sampling density).

At 1804, SAFT is performed to the collected measurement data resulting in focused SAFT data with three spatial dimensions. At $1806_B$, signal analysis is performed along the depth dimension, which results in the analytic measured data (e.g., an image of the phase). Concurrently, at $1806_A$, signal analysis is performed along the time dimension, which results in the analytic measured data (e.g., an image of the phase). This way, an image with SAFT and an image without SAFT are generated. Additional signal metrics, such as M1, M2/M1, P1, Cos P1, etc., may also be analyzed in the same steps.

At $1808_A$ and $1808_B$, disposition of the bond may be performed. The final result is an image (or images) useful for locating and sizing unbonds. For rendering the phase to a screen, a user of the UT technique may rotate the phase for a healthy bond from some angle $\phi$ to zero (0-degrees). This way, the phase for an unbond becomes $\pi$ (180-degrees). A user may also combine magnitude and phase for a compact and meaningful image representation of bond quality to the screen.

Figure 19:
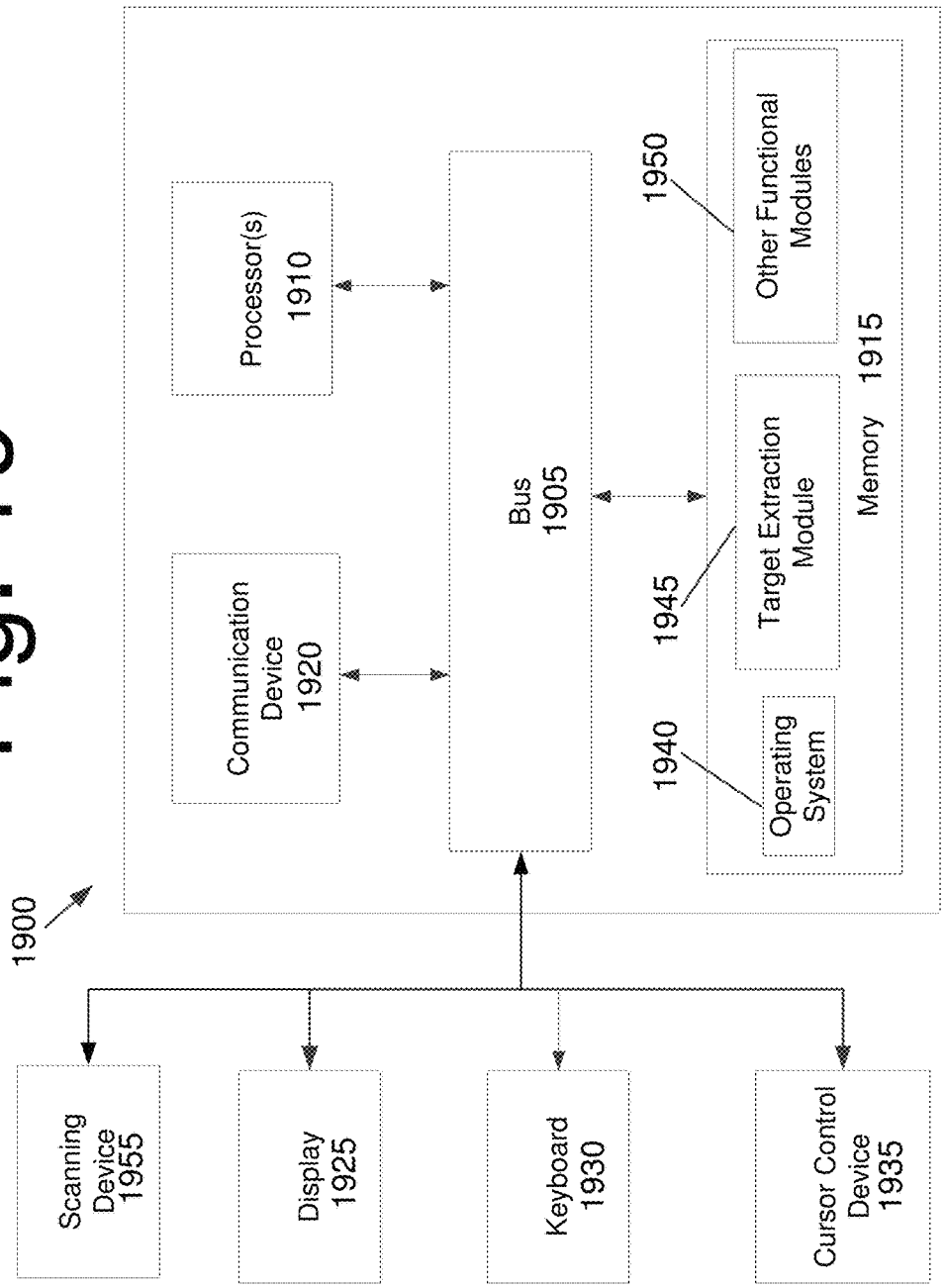
FIG. 19 is a block diagram illustrating a computing system for generating a waveform or one or more images of a bond quality, according to an embodiment of the present invention.

FIG. 19 is a block diagram illustrating a computing system (or system) for generating a waveform of one or more images to show the bond quality, according to an embodiment of the present invention. System 1900 includes a bus 1905 or other communication mechanism for communicating information, and processor(s) 1910 coupled to bus 1905 for processing information. Processor(s) 1910 may be any type of general or specific purpose processor, including a central processing unit ("CPU") or application specific integrated circuit ("ASIC"). Processor(s) 1910 may also have multiple processing cores, and at least some of the cores may be configured for specific functions. System 1900 further includes a memory 1915 for storing information and instructions to be executed by processor(s) 1910. Memory 1915 can be comprised of any combination of random access memory ("RAM"), read only memory ("ROM"), flash memory, cache, static storage such as a magnetic or optical disk, or any other types of non-transitory computer-readable media or combinations thereof. Additionally, system 1900 includes a communication device 1920, such as a transceiver, to wirelessly provide access to a communications network. Communication device 1920 may receive the signal including the targets. In some embodiments, communication device 1920 may also receive the signals of a scanning device 1955 including, but not limited to, the position of the transducer and whether transducer locations are of uniform density (i.e., automated scan) or non-uniform density (i.e., hand-scan).

Non-transitory computer-readable media may be any available media that can be accessed by processor(s) 1910 and may include both volatile and non-volatile media, removable and non-removable media, and communication media. Communication media may include computer-readable instructions, data structures, program modules or other data in a modulated data signal such as a carrier wave or other transport mechanism and includes any information delivery media.

Processor(s) 1910 are further coupled via bus 1905 to a display 1925, such as a Liquid Crystal Display ("LCD"), for displaying the waveform or images of the bond quality to a user or operator while the user or operator is scanning the TPS material with scanning device 1955. A keyboard 1930 and a cursor control device 1935, such as a computer mouse, are further coupled to bus 1905 to enable a user to interface with system 1900. However, in certain embodiments such as those for mobile computing implementations, a physical keyboard and mouse may not be present, and the user may interact with the device solely through display 1925 and/or a touchpad (not shown). Any type and combination of input devices may be used without deviating from the scope of the invention. Furthermore, in certain embodiments, such input devices are not present at all.

Memory 1915 stores software modules that provide functionality when executed by processor(s) 1910. The modules include an operating system 1940 for system 1900. The modules further include a waveform and image generation module 1945 that is configured to receive the bondline echo and the backwall echo and generate a waveform showing the bond quality. Waveform and image generation module 1945 may also generate a multitude of images, as shown in FIGS. 4-17, to show the bond quality between the TPS material and the composite. System 1900 may include one or more additional functional modules 1950 that include additional functionality.

One skilled in the art will appreciate that a "system" could be embodied as a personal computer, a server, a console, a personal digital assistant ("PDA"), a cell phone, a tablet computing device, or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large scale integration ("VLSI") circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Figure 20:
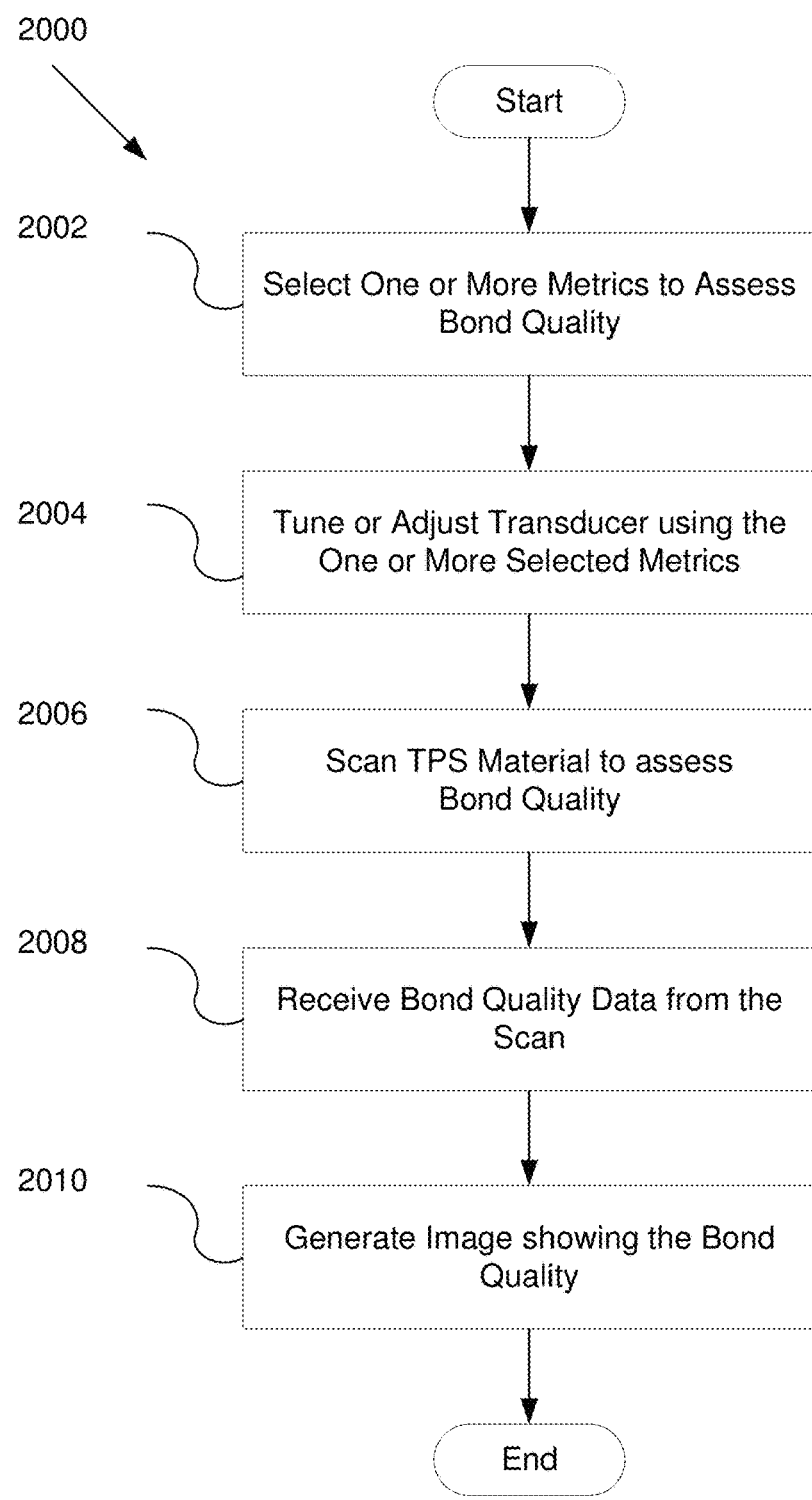
FIG. 20 is a flow diagram illustrating a process for assessing quality of the bond between TPS material and a composite, according to an embodiment of the present invention.

FIG. 20 is a flow diagram illustrating a process 2000 for assessing quality of the bond between TPS material and a composite, according to an embodiment of the present invention.

Process 2000 begins with a user (or operator) selecting one or more metrics to assess a bond quality between the TPS material and the composite at 2002. The metrics may include, but are not limited to: magnitude of bondline echo (M1), magnitude of backwall echo (M2), ratio of M1/M2, a phase of the bondline echo (P1), a phase of a cosine of the bondline echo (Cos P1), a weighted phase by the ratio of magnitudes (M2/M1)*(Cos P1), a weighted phase by the bondline echo magnitude (M1)*(Cos P1), pulse width, pulse energy, weighted pulse center, and/or after SAFT is applied to any of the above-identified metrics.

At 2004, depending on the embodiment, a scanning device, including a transducer, may be tuned or configured using the one or more selected metrics. For example, in some embodiments, by selecting the metrics in step 2004, the scanning device may be automatically configured for detection of the selected metrics when assessing the bond quality. At 2006, the TPS material is scanned to assess the bond quality. At 2008, bond quality data according to the selected one or more metrics is received by a computing device, and at 2010, the computing device may generate a waveform or one or more images, as shown in FIGS. 2-18, on a display.

It should be appreciated that steps 2006 to 2010 may be performed simultaneously in some embodiments. For example, as the user is scanning the TPS material with the scanning device, data associated with the bond quality is transmitted to the computing device and displayed on a display of the computing device. This way, a user or one or more technical analysts may be able to view or assess the bond quality in real-time. This will also allow the user or technical analyst to deduce where the gaps or unbonds are located.

FIG. 21 is a diagram illustrating a hand-held scanning system 2100, according to an embodiment of the present invention. To collect ultrasonic data and transducer position, a hand-held scanning technique may be used for curved surfaces, ease of use, and ease of calibration. Hand-held scanning system 2100 includes a first string encoder 2102A and a second string encoder 2102B, both of which are connected to a single ultrasonic contact transducer (or transducer) 2104, as shown in FIG. 21. The hand-held scanning system may scan relatively flat surfaces with any orientation (i.e., vertical, horizontal, etc.). In other embodiments, the position tracking may be performed by laser tracking, etc.

Determining Position for Hand-Held Scanning System

For purposes of explanation, system 2100 in some embodiments works by trilateration, since the output of both string encoders $2102_A$, $2102_B$ is a voltage proportional to the distance of the string between encoders $2102_A$, $2102_B$ and transducer 2104. The voltage corresponding to the $i^{th}$ encoder $v_i$ is the voltage scale per unit distance ($s_i$) times the distance between the encoder position ($m_i$) and the transducer position (p) plus the voltage offset ($o_i$) as defined by $$v_i = s_i |m_i - p| + o_i \qquad \text{Equation (1)}$$

where lowercase bold letters indicate a vector quantity. In some embodiments, a user may want the transducer position (p) in Cartesian (x, y) coordinates from the input voltages, as defined by $$p = \hat{x} p_x + \hat{y} p_y = p(v) \qquad \text{(Equation 2)}$$

where v is the vector for measured voltages, as defined by $$v = [v_1, v_2] \qquad \text{Equation (3)}$$

and p(v) represents the function relating input voltage to transducer position. The description of this function follows using the following equations.

First, the distance (a) between encoders may be computed and defined by $$d = |m_2 - m_1| \qquad \text{Equation (4)}$$

The distance (radii) between the transducer and each encoder may be computed from the measured voltage, as defined by $$r_1 = (v_1 - o_1)/s_1 \qquad \text{Equation (5)}$$

$$r_2 = (v_2 - o_2)/s_2 \qquad \text{Equation (6)}$$

(x', y') coordinates may be computed relative to a local coordinate system relative to the encoders, as defined by $$x' = \frac{(d^2 + r_1^2 - r_2^2)}{2d} \qquad \text{Equation (7)}$$

$$y' = -\sqrt{r_1^2 - (x')^2} \qquad \text{Equation (8)}$$

which assumes that the transducer may be below the encoders. The local encoder coordinate system may be given by $$\hat{x}' = \text{unit}(\hat{x}(m_{2x} - m_{1x}) + \hat{y}(m_{2y} - m_{1y})) \qquad \text{Equation (9)}$$

$$\hat{y}' = \text{unit}(\hat{x}(m_{1y} - m_{2y}) + \hat{y}(m_{2x} - m_{1x})) \qquad \text{Equation (10)}$$

$$\text{unit}(a) = a/|a| \qquad \text{Equation (11)}$$

where, unit( ) is a shorthand notation of a function that computes the unit vector for some input vector in some embodiments. Finally, $$p = \hat{x}' x' + \hat{y}' y' \qquad \text{Equation (12)}$$

In certain embodiments, the above process may be modified when the transducer is above the encoders by replacing the definition of y' with:

$$y' = \sqrt{r_1^2 - (x')^2} \qquad \text{Equation (13)}$$

Calibrating Hand-Held Scanning System

The previous section gave relationships v=v(p) and p=p(v). The positioning system may be defined by the voltage scale per unit distance ($s_i$), the encoder positions ($m_i$), and the voltage offset ($o_i$). For purposes of explanation, the vector a may be defined to describe the system parameters. The calibration process may consider one or more of the eight system parameters as unknowns and may determine the system parameters from a select number (N) calibration positions. These calibration positions ($c_k$ where k=1 ... N) are arbitrary in some embodiments. In other embodiments, however, these calibration positions are selected to span the area of interest. At each calibration position, the calibration voltage ($w_k$) may be measured. An objective cost function may be defined to represent the difference between calibration voltages ($w_k$) and voltages produced by estimating the system ($v_k(\sigma, c_k)$).

$$\text{cost}(\sigma) = \sum_{k=1}^{N} |w_k - v_k(\sigma, c_k)|^2 \qquad \text{Equation (14)}$$

Thus, the result of calibration is the result of minimizing the objective cost function, as defined by $$\sigma_c \rightarrow \text{minimize cost}(\sigma) \qquad \text{Equation (15)}$$

Data Synthesis From Nonuniform Hand-Scanned Data

In order for the data to be assembled into a meaningful image, the stream of information including position and ultrasonic data should first be synthesized. After synthesis, the resulting dataset is uniformly sampled along three dimensions: two for spatial coordinates (e.g., x and y) and one for time (t). In some embodiments, the following algorithm may be used both for real-time and offline computation.

The algorithm may aggregate hand-scan, spatially non-uniformly-sampled data $h_l[t]$ measured at positions ($x_l, y_l$) onto uniformly sampled data u[x,y,t]. The square brackets indicate that the quantity is discretely sampled and not a continuous function. The algorithm may use "Gaussian gridding" to aggregate data (d) and weight (w), as defined by $$d[x, y, t] = \sum_{l} h_l[t] g(x - x_l, y - y_l) \qquad \text{Equation (16)}$$

$$w[x, y] = \sum_{l} g(x - x_l, y - y_l) \qquad \text{Equation (17)}$$

where g(x,y) is a Gaussian basis function with tunable width ($\delta$), as defined by $$g(x, y) = \exp\left(\frac{-x^2}{\delta^2}\right) \exp\left(\frac{-y^2}{\delta^2}\right) \qquad \text{Equation (18)}$$

By definition, g(x,y) may be unbounded and continuous. In other embodiments, however, g(x,y) computation may be limited to a number of samples in each coordinate direction or represent a different basis function. These may also be tunable parameters. Finally, the uniform output data may be expressed as follows $$u[x, y, t] = \begin{cases} d[x, y, t]/w[x, y] & w[x, y] \geq \text{tol} \\ 0 & \text{otherwise} \end{cases} \qquad \text{Equation (19)}$$

for some weight tolerance (tol). In certain embodiments, the tunable width ($\delta$) is set to the transducer radius and the tolerance (tol) is 0.1. Effectively, the algorithm is a convolution of the nonuniform data with the Gaussian basis function normalized by a convolution of ones (1's) with the same Gaussian basis function.

The advantages of such an algorithm include, but are not limited to: tunable blurring, tunable tolerance, time invariance, iterative aggregation, and the calculation complexity is proportional to the number of spatial samples or O(N). Other algorithms such as mesh-based algorithms have a computational complexity proportional to the square of the number of spatial samples or $O(N^2)$, which is considerably slower. By using the algorithm described herein, the real-time reconstruction performs the convolution iteratively, whereas an offline reconstruction performs the same convolution monolithically. In further embodiments, measurement positions ($x_l, y_l$) may be rotated or translated to accommodate a particular geometry.

SAFT

SAFT may be used online or offline to maximize the final image contrast and resolution. Additionally, some spatial averaging of the material occurs, which reduces the effects of material inhomogeneity. The result is a volume image such that each volumetric pixel (i.e., voxel) is a result of the mathematical (i.e., synthetic) focusing of multiple measurement locations. Moreover, the algorithm may implement "Stolt interpolation" by using nonuniform fast Fourier transform (NFFT) to provide fast and accurate results without the need to compute the SAFT image for the entire unambiguous range.

The algorithm may begin with the data resulting from data synthesis, u[x,y,t]. In certain embodiments, the time domain may be translated into the temporal frequency domain, as defined by $$U'[x,y,f] = FFT_t\{u[x,y,t]\} \qquad \text{Equation (20)}$$

where $FFT_t$ computes the FFT along the last dimension. Next, frequencies of interest may be bandpass filtered (bpf), as defined by $$U[x,y,f] = bpf\{U'[x,y,f]\} \qquad \text{Equation (21)}$$

For example, a user may only want to preserve frequencies from 30 kHz to 800 kHz since the transducer center frequency is about 500 kHz. Then, the spectral decomposition (S), which is a 2D spatial FFT along x and y, may be computed using the following $$S[k_x, k_y, f] = FFT_{xy}\{U[x,y,f]\} \qquad \text{Equation (22)}$$

After that, the dispersion relation may be used to determine $k_z$ and $k_z$ may be used for S, as follows $$k_z = k_z(f) = \sqrt{\left(\frac{4\pi f}{v}\right)^2 - k_x^2 - k_y^2} \qquad \text{Equation (23)}$$

$$S[k_x, k_y, f] \rightarrow S[k_x, k_y, k_z] \qquad \text{Equation (24)}$$

where v is the speed of sound in the TPS material, which may be similar to the speed of sound in water. In this example, S is uniformly sampled in f, and now it can also be nonuniformly sampled in $k_z$. With that being said, subsequent Fourier transforms on nonuniform data may use the NFFT instead of the FFT. Finally, the inverse Fourier transform may be performed on all three spatial dimensions to obtain the final volume image (s), as defined by $$s[x,y,z]=FFT_{xy}^{-1}\{NFFT_z^{-1}\{S[k_x,k_y,k_z]\}\}$$ Equation (25)

Automatic Gating

In some cases, panels may require automatic gating of the signal, where the TPS material and the composite thicknesses vary greatly. It should be noted that automatic gating may be performed in time on u[x, y, t] or in space on the SAFT image s[x, y, z] without losing generality.

For this, the following algorithm described below may use u[x, y, t], for example. The algorithm may take advantage of the fact that the thickness variation is predominantly along only one coordinate direction—radially outward from the center of the heat shield. Consequently, the algorithm can be made to be less sensitive to noise—a distinct advantage—by summing the absolute value of the analytic signal over the spatial dimension that does not require automatic gating. The algorithm may be executed as discussed below. First, the hand-scan data $h_i[t]$ in space is rotated to align the gate variation along the y-axis. Second, hand-scan data synthesis is performed to obtain u[x, y, t]. Third, the absolute value of the analytic signal along x is summed to obtain a[y, t]. Fourth, for every y, the location of the first maximum is identified in a[y, t] along t resulting in the indices ($i_{max}$[y]) and values ($v_{max}$[y]). Fifth, insignificant values are culled in $v_{max}$[y] and their respective indices resulting in $i'_{max}$[y] and $v'_{max}$[y]. From these indices, first minimum is found along t resulting in $i_{min}$[y] and $v_{min}$[y]. Insignificant minimums are culled, these insignificant minimums generally occur too close to $i'_{max}$[y] resulting in $i'_{min}$[y] and $v'_{min}$[y]. Consequently, $i'_{mm}$[y] represents the boundary between the first and second pulses. However, the current estimate of the boundary may vary wildly, is not contiguous, and is susceptible to noise. Next, a N-point cubic spline is fitted to $i'_{min}$[y]. N-point cubic spline represents the gate boundary between the bondline echo and the backwall echo—to be used when computing metrics.

For later reference, gates are defined in some embodiments as $G_1=[G_{11}, G_{12}]$ and $G_2=[G_{21}, G_{22}]$, where G## represents the gate boundary in time (t) or space (z).

It should be noted that panels on the radius of the heat shield may serve as good examples where automatic gating is necessary. The panel has particularly thin TPS material in its center.

Signal Metrics

Various signal metrics may be extracted to quantify the bondline. Metrics may be used either singly or by combination to combat the inhomogeneity in the specimen and the complexity of the reflection due to unbonds, thick epoxy, porosity, etc. See, for example, Table 1, which shows all the metrics used with their description.

TABLE 1

Extracted Signal Features

| Symbol | Signal Feature |
|---|---|
| $M_1$ | Magnitude of the bondline echo |
| $M_2$ | Magnitude of the backwall echo |
| $\phi_1$ | Phase of the bondline echo, an indication of bond quality (good ≈ 0, bad ≈ π) |
| $T_1$ | Time of flight of the bondline echo (μs), specific to reconstruction before SAFT, proportional to $Z_1$ |
| $Z_1$ | Depth of bondline echo (mm), specific to reconstruction after SAFT, proportional to $T_1$ |

TABLE 1-continued

Extracted Signal Features

| Symbol | Signal Feature |
|---|---|
| $W_1$ | Width of the pulse, an indication of multiple features occurring simultaneously under the transducer face, proportional to porosity |
| $M_2/M_1$ | Magnitude ratio, less susceptible to AVCOAT inhomogeneity. |
| $\cos(\phi_1)$ | Negative at unbond, otherwise positive |
| $(M_2/M_1)\cos(\phi_1)$ | Magnitude ratio polarized by the sign of the bondline phase and darkened when phase is not clearly bond or unbond |
| $M_1 \text{sign}(\cos(\phi_1))$ | Magnitude of the bondline echo polarized by the sign of the bondline phase |
| $M_1 \cos(\phi_1)$ | Magnitude of the bondline echo polarized by the sign of the bondline phase and darkened when phase is not clearly bond or unbond |

The metrics may be extracted similarly for both u[x, y, t] and s[x, y, z], without losing generality. The metrics may use the analytic representation of the signal, which is the signal after all negative frequencies are removed. To compute the analytic signal, the FFT may be performed along time, as defined by $$U[x,y,f]=FFT_t\{u[x,y,t]\}$$ Equation (26)

Next, all negative frequencies may be eliminated by using a positive frequency filter (pff), as defined by $$\underline{U}[x,y,f]=pff\{U[x,y,f]\}$$ Equation (27)

Finally, the signal may be casted back into time by performing the inverse FFT along time, as defined by $$\underline{u}[x,y,t]=FFT_t^{-1}\{\underline{U}[x,y,f]\}$$ Equation (28)

Thus, $\underline{u}$[x, y, t] may be the analytic signal representation of u[x, y, t].

For $M_1$ and $M_2$, the fundamental metric may be the maximum magnitude of the analytic signal within the respective gate, as defined by $$M_1=\max|\underline{u}[x,y,t]|G_{11}\leq t\leq G_{12}$$ Equation (29)

$$M_2=\max|\underline{u}[x,y,t]|G_{21}\leq t\leq G_{22}$$ Equation (30)

For this, the corresponding location of $M_1$ and $M_2$ is $t_1$ and $t_2$, respectively. See the following equation below.

$$T_1=t_1$$ Equation (31)

The phase of the analytic signal at the location of $M_1$ may be a good representation of the shape, as defined by $$\phi_1=\text{angle}\{\underline{u}[x,y,t_1]\}$$ Equation (32)

Given $M_1$, $M_2$, and $\phi_1$, the following metrics may be computed—$M_2/M_1$, $\cos(\phi_1)$, $(M_2/M_1) \cos(\phi_1)$, $M_1 \text{sign}(\cos(\phi_1))$, and $M_1 \cos(\phi_1)$. The last metric is the width of the pulse. This last metric may compute the area of the energy (i.e., square) of the analytic pulse and may determine the closest rectangular width, as defined by $$W_1 = \frac{\Delta t \sum_{t=G_{11}}^{G_{12}} |\underline{u}[x,y,t]|^2}{\max|\underline{u}[x,y,t]|^2 \,|\, G_{11} \leq t \leq G_{12}}$$ Equation (33)

Embodiments described herein allow for the detection of an air gap in the bondline, i.e., air between TPS material and the composite. Embodiments may also allow for the detection of an unbond, i.e., when the TPS material and the composite are touching but not bonded. Porosity may also be detected in some embodiments as a bulk property even though the operating wavelength is too large for the porosity itself.

Certain embodiments may include a technique that uses ultrasound to inspect bonds between thick, dissimilar, attenuative, or scattering materials. This technique may generate an image, combined from phase and amplitude of the analytical signal. The shape of the echo signal may reveal the presence of the bond more reliably than magnitude for these materials, while the magnitude returning from an attenuative medium relates to the confidence level of the measurement.

The shape of the signal can be quantified several ways. For example, the phase may be defined by complex instantaneous phase of the analytic signal at peak echo magnitude. For reference, the analytical signal is the complex representation of a waveform signal without negative frequency components.

The phase of the signal is useful since the phase of the signal is a strong function of the interfaces from which a UT pulse is reflected. For example, the phase of the signal for a well bonded TPS to a substrate of higher mechanical impedance is some angle $\phi$. The phase of the signal for an unbond/debond would be close to $\phi+\pi$ since air due to the unbond/debond has a much lower impedance than the TPS or the substrate. This difference is the polar opposite, which is the largest difference possible, and is only related to the mechanical impedance of the media.

It should be appreciated that variables, such as transducer, instrumentation and other conditions, remain constant. Other conditions may include thicker TPS materials, ramped or nonplanar TPS materials, thick bondline, thin composite, and more.

Lastly, phase of the signal may be combined with other signal metrics to produce more meaningful images for disposition. As discussed above, the amplitude of the echo relates to the confidence level of the measurement. Measuring phase from a low amplitude signal is more influenced by noise, while a strong signal gives a more definitive measurement of phase. Furthermore, taking ratios of echo signals returning from different interfaces normalize the unwanted effects of the irregular medium, provided that both echo signals traversed the same medium. Consequently, by applying a sequence of signal processing steps to the raw signal, using information of the phase and amplitude in a very meaningful way, makes a very difficult inspection of a bonded joint possible.

It should be appreciated that embodiments described herein allow a user to perform a free hand scan, resulting in high precision images. It should be further appreciated that the embodiments are not limited to the aerospace industry, but may also be applicable to a variety of industries, including but not limited to, medical.

It will be readily understood that the components of various embodiments of the present invention, as generally described and illustrated in the figures herein, may be arranged and designed in a wide variety of different configurations. Thus, the detailed description of the embodiments of the systems, apparatuses, methods, and computer programs of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. An apparatus for assessing a bond quality, comprising:
a highly damped transducer emitting an incident wave, traversing through thermal protection system (TPS) material and to a back wall of a composite, wherein
the incident wave is a low frequency signal, and returns a bondline echo when the incident wave reaches a bondline and returns a backwall echo when the incident wave reaches the backwall of the composite to generate a waveform on a computing system assessing the bond quality between the TPS material and the composite and revealing possible unbonds or kissing unbonds.

2. The apparatus of claim 1, wherein
the computing system is configured to extract a magnitude of the bondline echo and a magnitude of the backwall echo from the generated waveform, and generate an image of the magnitude of the bondline echo and an image of the magnitude of the backwall echo to assess the bond quality.

3. The apparatus of claim 2, wherein
the computing system is further configured to enhance the image showing the bond quality by taking a ratio of a signal amplitude between the magnitude of the bondline echo and the magnitude of the backwall echo.

4. The apparatus of claim 2, wherein
the computing system is further configured to enhance the image showing the bond quality by taking a phase of a complex analytic signal corresponding to a location of the magnitude of the bondline echo.

5. The apparatus of claim 4, wherein
the computing system is further configured to enhance the image of the phase by implementing a cosine of the phase of the bondline echo revealing any kissing unbonds in the bondline.

6. The apparatus of claim 2, wherein
the computing system is further configured to enhance the image by implementing a weighted phase of a bondline echo magnitude ratio revealing any kissing unbonds in the bondline.

7. The apparatus of claim 2, wherein
the computing system is further configured to enhance the image by implementing a weighted phase of a bondline echo magnitude revealing any kissing unbonds in the bondline.

8. The apparatus of claim 1, further comprising:
the computing system is further configured to apply a synthetic aperture focusing technique to one or more metrics that are received from the highly damped transducer to reveal any unbonds in the bondline.

9. A process for assessing the quality of a bond between a thermal protection system (TPS) and a composite, comprising:
configuring a highly damped transducer with low frequency to assess the quality of the bond with one or more metrics;
scanning, by the highly damped transducer, the TPS material to assess the quality of the bond; and
generating, by a computing system, a waveform, one or more images, or both, identifying the quality of the bond according to the one or more selected metrics.

10. The process of claim 9, wherein the one or more metrics comprises a magnitude of a bondline echo, a magnitude of a backwall echo, a ratio of the magnitude of the bondline echo and the magnitude of the backwall echo, a weighted phase by the ratio of the magnitude, a weighted phase by the magnitude of the bondline echo, a pulse width, a pulse energy, a weighted pulse center, or any combination thereof.

11. The process of claim 9, wherein the waveform, the one or more images, or both, reveal one or more gap locations or one or more unbond locations in the bond.

12. The process of claim 9, wherein the configuring the highly damped transducer comprises determining a position of the highly damped transducer by trilateration with a set of encoders.

13. The process of claim 9, wherein the configuring of the highly damped transducer positioning system comprises determining one or more unknown system parameters from a select number of calibration positions, wherein
the calibration positions comprise an area of interest for scanning the bond.

14. The process of claim 13, wherein the configuring of the highly damped transducer positioning system further comprises measuring a calibration voltage for each calibration position.

15. The process of claim 14, wherein the generating of the waveform, the one or more images, or both, comprises
synthesizing data comprising position data and ultrasonic data received from the highly damped transducer and positioning system; and
uniformly sampling the synthesized data along three dimensions, the three dimensions comprise x- and y-spatial coordinates and time.

16. The process of claim 14, wherein the generating of the waveform, the one or more images, or both, comprises applying a synthetic aperture focusing technique (SAFT) to the data to generate one or more non-color or color images to maximize contrast and resolution revealing one or more gap locations or one or more unbond locations in the bond.

17. A hand-held scanning system for assessing a quality of a bond between a thermal protection system (TPS) and a composite, the hand-held scanning system comprises:
a set of string encoders connected to a highly damped transducer, wherein
the transducer is configured to scan the TPS having a flat surface, curved surface, or both, for purposes of assessing the quality of the bond; and
a computing system configured to receive the scanned data and generate a waveform, one or more images, or both, revealing one or more locations of a gap or one or more locations of an unbond in the bond.

18. The hand-held scanning system of claim 17, wherein the transducer is configured to transmit an incident wave past a bondline located between the TPS and the composite to a backwall of the composite.

19. The hand-held scanning system of claim 18, wherein the computing system is configured to receive a bondline echo when the incident wave reaches the bondline, and receive a backwall echo when the incident wave reaches the backwall.

20. The hand-held scanning system of claim 19, wherein the computing system uses the bondline echo and the incident wave to produce a waveform or one or more non-color or color images revealing the gap in the bond or the unbond in the bond.

* * * * *